(12) United States Patent
Kaji

(10) Patent No.: US 6,939,454 B2
(45) Date of Patent: Sep. 6, 2005

(54) CHIP TYPE ELECTROPHORESIS DEVICE

(75) Inventor: Toru Kaji, Kyoto (JP)

(73) Assignee: Shimadzu Corporation, Kyoto (JP)

(*) Notice: Subject to any disclaimer, the term of this patent is extended or adjusted under 35 U.S.C. 154(b) by 392 days.

(21) Appl. No.: 10/289,382

(22) Filed: Nov. 7, 2002

(65) Prior Publication Data
US 2003/0094370 A1 May 22, 2003

(30) Foreign Application Priority Data
Nov. 22, 2001 (JP) .................. 2001-358419

(51) Int. Cl.$^7$ .................................. G01N 27/453
(52) U.S. Cl. ............................. 204/604; 204/601
(58) Field of Search .......................... 204/601–604, 204/451–455

(56) References Cited
U.S. PATENT DOCUMENTS 6,132,579 A * 10/2000 Edwards et al. ............ 204/451
6,375,817 B1 * 4/2002 Taylor et al. ............... 204/453

* cited by examiner

Primary Examiner—Alex Noguerola
(74) Attorney, Agent, or Firm—Manabu Kanesaka

(57) ABSTRACT

An electrophoresis chip is formed of a pair of transparent base plates. A sample introduction flow path and a separation flow path crossing each other are formed on a surface of one of the base plates, and the other base plate is provided with a separation buffer waste, a separation buffer reservoir, a loading buffer reservoir, and a loading buffer waste, which are formed as through holes at positions corresponding to ends of the flow paths. Further, a sample reservoir for injecting a sample therein is formed as a through hole on the sample introduction flow path at a position different from that of the loading buffer reservoir. Electrodes are disposed at the separation buffer waste, the separation buffer reservoir, the loading buffer reservoir, and the loading buffer waste. The electrode is not disposed at the sample reservoir.

8 Claims, 4 Drawing Sheets

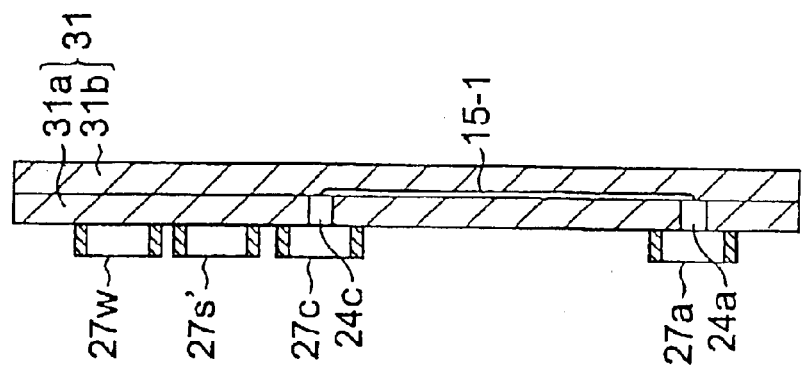
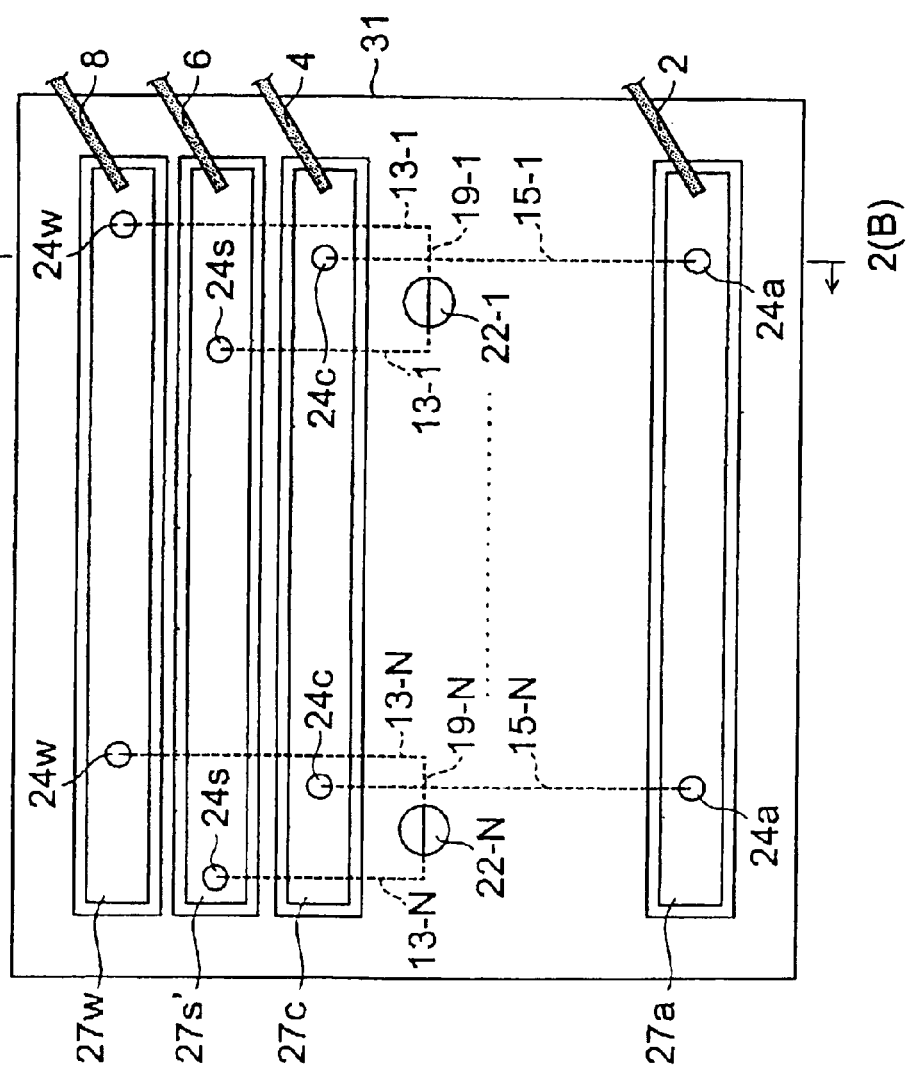

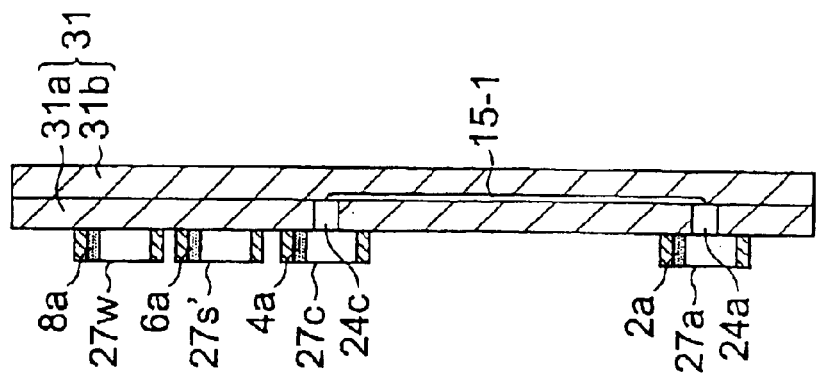
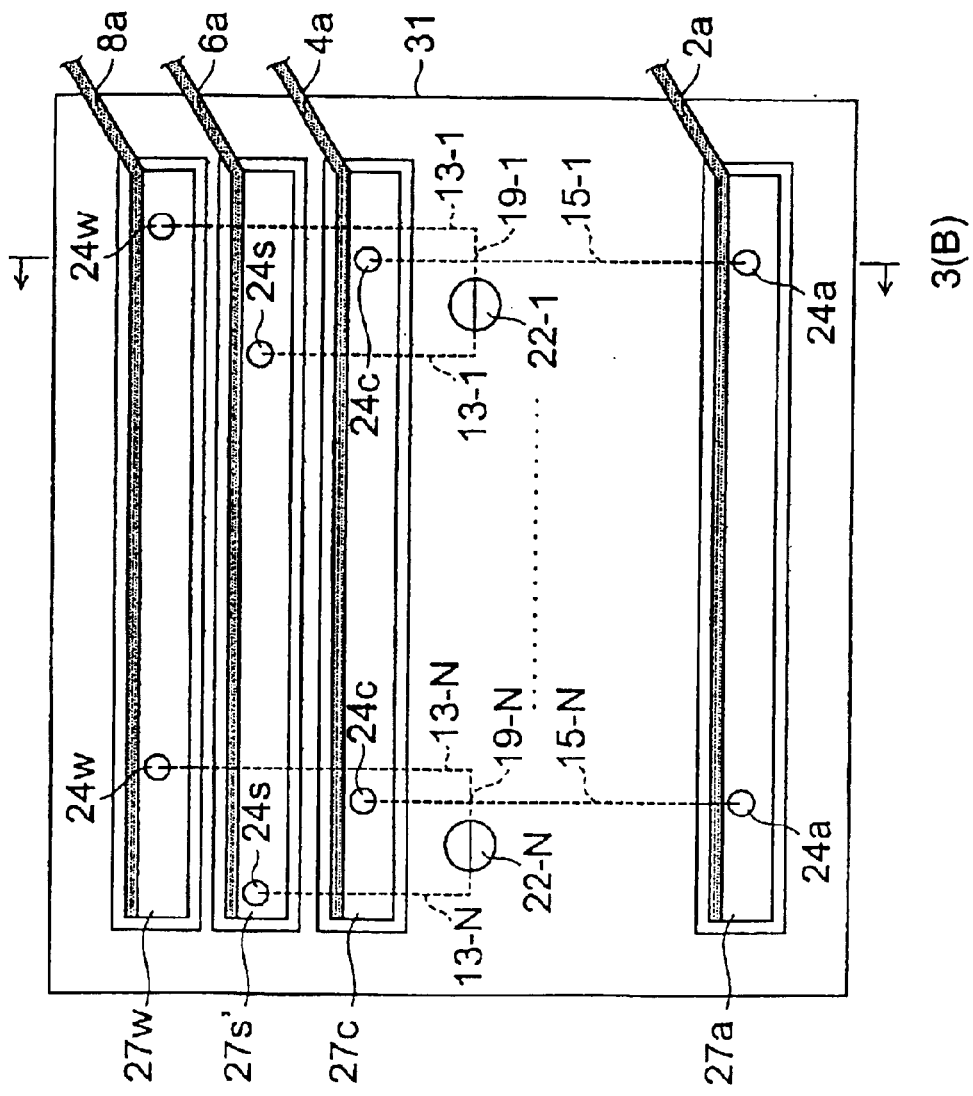

US 6,939,454 B2

CHIP TYPE ELECTROPHORESIS DEVICE

BACKGROUND OF THE INVENTION AND RELATED ART STATEMENT

The present invention relates to a chip type electrophoresis device for analyzing a sample containing an extremely small amount of a protein, nucleic acid, a drug, or the like at a high speed with a high resolution.

In a case that an extremely small amount of a protein or nucleic acid is analyzed, conventionally an electrophoresis has been used, and a capillary electrophoresis has been known as a typical method of the electrophoresis. In the capillary electrophoresis, a matrix for separation (an electrophoresis medium) is charged in a glass capillary (hereinafter simply referred to a capillary) having an inner diameter of 100 μm. A sample is introduced into one end of the capillary, and both ends of the capillary contacts a buffer solution. Then, a high voltage is applied between both ends of the capillary through the buffer solution to thereby develop the sample in the capillary. Since the capillary has a large surface area relative to a volume thereof, that is, the capillary has a high cooling effect, a high voltage can be applied thereto, and an extremely small amount of sample such as DNA (deoxyribonucleic acid) can be analyzed at a high speed with a high resolution.

However, the capillary is easily broken because of a very small outer diameter of about 100 to 500 μm, causing a problem that the capillary is not easy to handle when replacing. Also, there may be a case that the heat radiation may not be sufficient to apply a higher voltage, resulting in a negative effect on a state of sample separation. Further, since the voltage is applied to both ends of the capillary through the buffer solution, the capillary is required to have at least enough length to contact the buffer solution, so that the capillary is required to have a length longer than a certain length.

Therefore, instead of the capillary, there has been proposed an electrophoresis chip formed by bonding two base plates as disclosed in D. J. Harrison et al, Anal. Chem. (1993), 283, 361–366, as a device expected to carry out a high-speed analysis and to reduce a size of the device. An example of the electrophoresis chip is shown in FIGS. 4(A) to 4(C).

An electrophoresis chip 11 is formed of a pair of base plates 11a, 11b having a transparent plate shape formed of an inorganic material. Electrophoresis capillary grooves (channels) 13, 15 crossing each other are formed on a front surface of one base plate 11b, and the other base plate 11a is provided with through holes as a separation buffer waste 17a, a separation buffer reservoir 17c, a sample reservoir 17s, and a loading buffer waste 17w, which are formed at positions corresponding to ends of the channels 13 and 15. The base plates 11a and 11b are laminated and bonded to form the electrophoresis chip 11 as shown in FIG. 4(C).

When the electrophoresis is conducted by using the electrophoresis chip 11, the electrophoresis medium is charged from one of the reservoirs and the wastes to fill the channels 13 and 15, the reservoirs 17c, 17s and the wastes 17a, 17w. Then, the electrophoresis medium in the reservoirs 17c, 17s and the wastes 17a, 17w is removed therefrom. Thereafter, the sample is injected from the sample reservoir 17s corresponding to one end of the relatively shorter channel (a sample introduction flow path) 13, and the buffer solution is injected to the other reservoir 17c and the wastes 17a, 17w.

After the electrophoresis medium, the sample, and the buffer solution are injected, the electrophoresis chip 11 is attached to an electrophoresis device, and a predetermined voltage is applied to the respective reservoirs 17c, 17s and the wastes 17a, 17w, so that the sample is migrated in the channel 13 to be led to an intersecting portion 19 where the channels 13 and 15 cross each other. Then, the voltage applied to the respective reservoirs 17c, 17s and the wastes 17a, 17w, is switched, and due to the voltage between the reservoir 17c and the waste 17a located at both ends of the relatively longer channel (a separation flow path) 15, the sample in the intersecting portion 19 is migrated into the channel 15. Thereafter, the sample remained in the reservoir 17s is substituted by the buffer solution. Then, the voltage for the electrophoresis is applied to the respective reservoirs 17c, 17s and the wastes 17a, 17w, and the sample injected in the channel 15 is separated therein. By providing a detector at an adequate position on the channel 15, the sample separated by the electrophoresis can be detected.

The reservoirs 17c, 17s and the wastes 17a, 17w are respectively provided with electrodes. These electrodes are in a rod form and may be inserted in the reservoirs and the wastes at the time of analysis, or may be attached thereto by a vapor deposition. Since it is necessary to fill the sample reservoir 17s with an enough amount of the sample to allow the electrode to be soaked sufficiently therein, it is difficult to reduce the amount of the sample.

Further, when the sample contacts the electrode in order to apply the voltage for introducing the sample into the flow path, the electrolysis occurs. If the amount of the sample is small, it is possible that the electrolysis affects the analysis. Therefore, in order to suppress the effect of the electrolysis, it is also necessary that the sample reservoir have a volume more than a predetermined amount. In view of the foregoing, it is also difficult to reduce the amount of the sample.

Accordingly, an object of the invention is to provide a chip type electrophoresis device that can analyze a sample even if an amount of the sample is very small.

Further objects and advantages of the invention will be apparent from the following description of the invention.

SUMMARY OF THE INVENTION

A chip type electrophoresis device of the invention is provided with a sample reservoir disposed at a separation flow path or a sample introduction flow path crossing the separation flow path for injecting a sample therein. In the chip type electrophoresis device of the invention, the sample reservoir is not provided with an electrode, and a voltage for introducing the sample is applied via electrodes disposed at portions other than the sample reservoir.

In the conventional electrophoresis device shown in FIGS. 4(A) to 4(C), the sample is injected into the sample reservoir, and the electrode is brought into contact with the sample in the sample reservoir to apply the voltage. In the present invention, however, although the sample is injected in the sample reservoir, the sample does not make direct contact with the electrode. Since the electrode is disposed in a separate reservoir, the sample reservoir is not required to have a large amount of the sample to allow the electrode to contact the sample securely, thereby eliminating an effect of the electrolysis. Therefore, it is possible to reduce the amount of the sample.

The reservoir provided with the electrode is not the sample reservoir but a reservoir in which a buffer is injected. Therefore, a capacity of the reservoir provided with the electrode can be increased to receive a large amount of the buffer in the reservoir, so that the effect of the electrolysis can be minimized. As described above, according to the present invention, reducing the amount of the sample can be achieved while minimizing the effect of the electrolysis.

The present invention also includes a case that the electrode is bonded to the chip by a vapor deposition in advance. In a case that the electrode is structured as a member separate from the chip and disposed at the electrophoresis device side, a position of the reservoir into which the electrode is inserted is restricted, and it may be required to provide the reservoir at a position distant from the separation flow path. In the present invention, however, since the sample reservoir and the electrode are separated, in the case that the electrode is formed as the member separate from the chip, the electrophoresis device becomes easier to design.

Also, in the chip side, the sample reservoir can be positioned various locations. For example, in case that the chip includes a sample introduction flow path joining the separation flow path, the sample reservoir can be disposed in the vicinity of the intersecting portion, where the separation flow path and the sample introduction flow path cross each other, at an upstream side of a direction of introducing the sample in the sample introduction flow path. Accordingly, an efficient sample introduction can be conducted.

The chip type electrophoresis device according to the present invention includes the electrophoresis device having the sample introduction flow path crossing the separation flow path, similar to the one shown in FIGS. 4(A) to (C). Also, the chip type electrophoresis device of the invention includes a device having only a separation flow path in which a sample reservoir is provided at one end of the separation flow path, or a device in which a single chip is provided with a plurality of separation flow paths.

BRIEF DESCRIPTION OF THE DRAWINGS

FIG. 2(A) is a plan view schematically showing an arrangement of flow paths and electrodes in another embodiment of the invention;

FIG. 2(B) is a sectional view taken along line 2(B)—2(B) in FIG. 2(A);

FIG. 3(A) is a plan view schematically showing an arrangement of flow paths and electrodes in still another embodiment of the invention;

FIG. 3(B) is a sectional view taken along line 3(B)—3(B) in FIG. 3(A); and

FIGS. 4(A)–4(C) are views showing a conventional electrophoresis chip, wherein FIG. 4(A) is a top plan view schematically showing one base plate of the conventional electrophoresis chip, FIG. 4(B) is a top plan view schematically showing the other base plate of the conventional electrophoresis chip, and FIG. 4(C) is a side view showing the conventional electrophoresis chip in a state that the base plates are laminated.

DETAILED DESCRIPTION OF PREFERRED EMBODIMENTS

Figure 1:
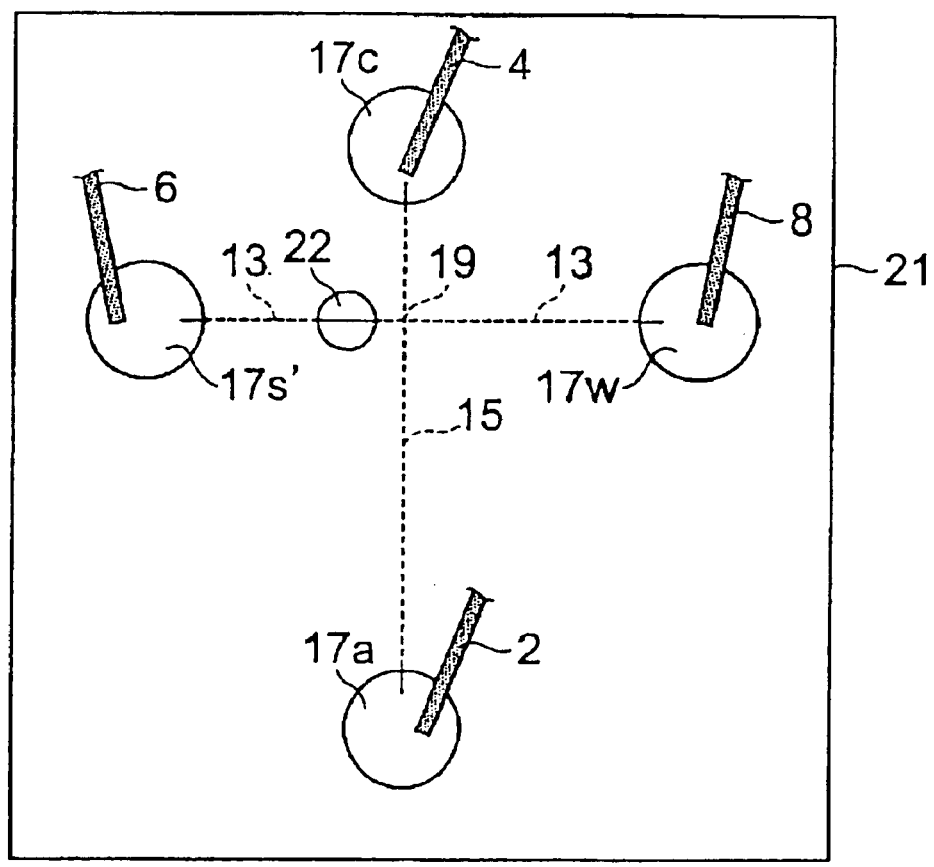
FIG. 1 is a plan view schematically showing an arrangement of flow paths and electrodes in a chip type electrophoresis device according to an embodiment of the invention.

FIG. 1 is a plan view schematically showing an embodiment of the invention. As in the conventional chip shown in FIGS. 4(A) to 4(C), an electrophoresis chip 21 comprises a pair of transparent base plates formed of an inorganic material (for example glass, quartz, and silicon) or a plastic. Also, electrophoresis capillary channels 13 and 15, which cross each other, are formed on a front surface of one of the base plates by photolithography for semiconductor manufacture, etching technology, or micro machining. Also, the same base plate or the other base plate is provided with through holes, which are formed at positions corresponding to the ends of the channels 13, 15 and constitute a separation buffer waste 17a, a separation buffer reservoir 17c, a loading buffer reservoir 17s', and a loading buffer waste 17w. Furthermore, a sample reservoir 22 for injecting a sample therein is formed as a through hole on the capillary channel 13 at a position separated from a position of the reservoir 17s'.

The through holes 17a, 17c, 17s', 17w, 22 may be formed in the base plate in which the channels 13, 15 are formed, or may be formed at the other base plate that faces and connects with the base plate provided with the channels. In case that the through holes 17a, 17c, 17s', 17w, 22 and the channels 13, 15 are formed in the same base plate, it is not necessary to align positions of the through holes 17a, 17c, 17s', 17w, 22 with the channels 13, 15, so that the chip can be produced more easily.

Figure 4A:
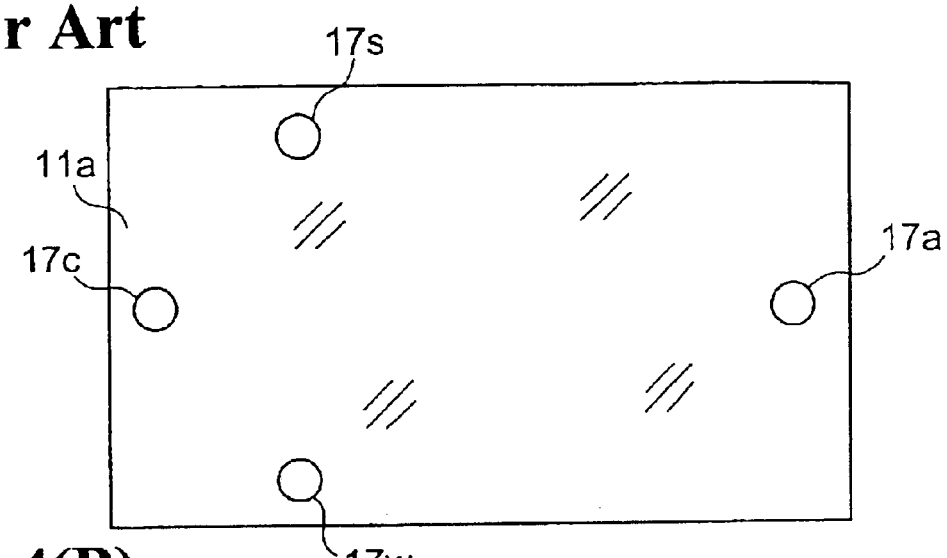
Figure 4B:
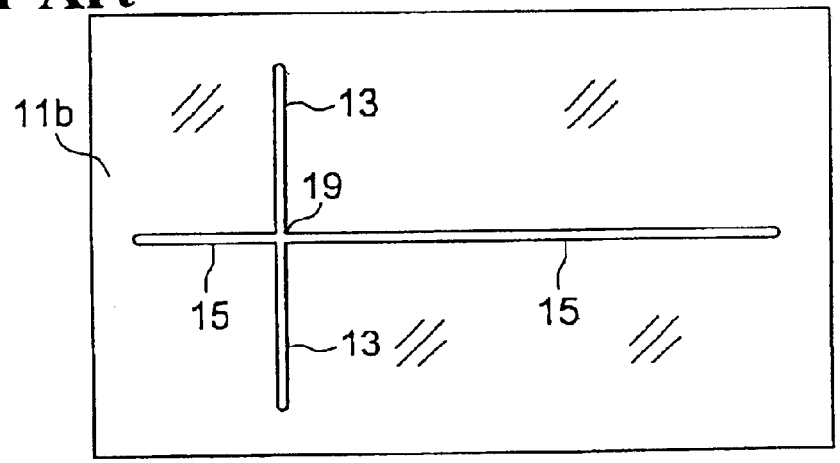
Figure 4C:
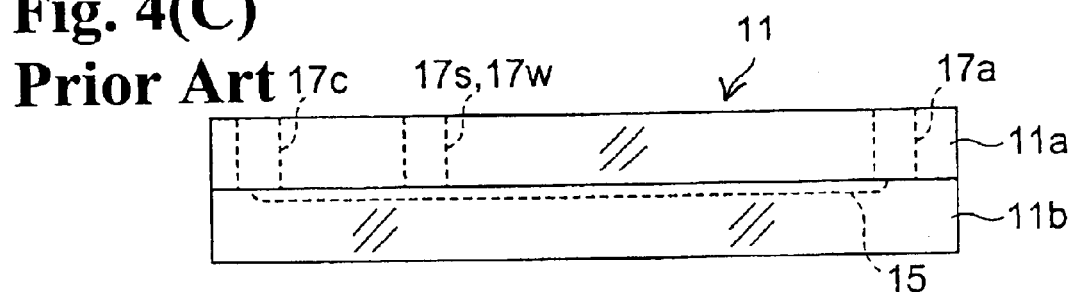

In the electrophoresis chip 21, as in the chip shown in FIGS. 4(A) and 4(C), the base plates are laminated and bonded, and the capillary channel 13 constitutes a sample introduction flow path and the capillary channel 15 constitutes a separation flow path.

As compared with the chip type electrophoresis device shown in FIGS. 4(A) to 4(C), the sample introduction flow path in the present invention is different. In the conventional electrophoresis device shown in FIGS. 4(A) to 4(C), the sample is injected into the sample reservoir 17s, and the electrode is also disposed in the sample reservoir 17s. On the other hand, in the embodiment of the invention, electrodes 6 and 8 are respectively disposed at the loading buffer reservoir 17s' and the loading buffer waste 17w formed at both ends of the sample introduction flow path 13. The sample is injected into the sample reservoir 22 disposed on the sample introduction flow path 13 at the position different from the position of the reservoir 17s'.

A direction of the electrophoresis for introducing the sample is a direction from the reservoir 17s' to the waste 17w, and the sample reservoir 22 is disposed at an upper stream side (a reservoir 17s' side) of the intersection portion 19, where the flow paths 13, 15 cross each other, on the sample introduction path 13. As the sample reservoir 22 is disposed close to the intersecting portion 19, the efficiency of introducing the sample is improved. Since the electrode is not disposed in the sample reservoir 22, even if the electrodes are structured separately from the chip and provided at the electrophoresis device side, the sample reservoir 22 can be installed at various positions with high flexibility, so that the sample reservoir 22 can be easily disposed at a position close to the intersecting portion 19.

Structural features of the electrophoresis chip 21 of the embodiment other than the reservoir 22 for introducing the sample and the loading buffer reservoir 17s' are the same as those in the conventional chip shown in FIGS. 4(A) to 4(C).

In case that the electrophoresis is conducted by using the electrophoresis chip 21, prior to the analysis, the electrophoresis medium is charged through the reservoirs 17c, 17s' or the wastes 17a, 17w, by pressure-feeding or pumping by a syringe, for example. That is, the electrophoresis medium is charged through the waste 17a into the flow paths 13, 15, the reservoir 17c, the wastes 17a, 17w. Similarly, the electrophoresis medium is charged through the reservoir 17s' into the reservoir 17s' and the flow path 13. As the electrophoresis medium, LPA (linear type polyacrylamide) or the like can be used. Then, the electrophoresis medium filled in the reservoirs 17c, 17s', and the wastes 17a, 17w is replaced with the buffer solution. If the electrophoresis medium is remained in the sample reservoir 22, the efficiency of introducing the sample is impaired. After the electrophoresis medium in the sample reservoir 22 is removed and the sample reservoir 22 is washed, the sample is injected into the sample reservoir 22.

After the electrophoresis medium, the sample, and the buffer solution are injected, the electrophoresis chip 21 is attached to the electrophoresis device. Alternatively, the electrophoresis medium, the sample, and the buffer solution may be injected while the electrophoresis chip 21 is attached to the electrophoresis device.

In introducing the sample, a predetermined voltage is applied to the respective reservoirs 17c, 17s' and the wastes 17a, 17w, and the sample is allowed to flow in the flow path 13 and reach the intersecting portion 19 where the flow paths 13, 15 cross each other.

Then, the voltage applied to the respective reservoirs 17c, 17s' and the wastes 17a, 17w is switched to a voltage for the electrophoresis, and the sample at the intersecting portion 19 is allowed to migrate in the separation flow path 15 to be separated. By providing a detector at an adequate position on the separation flow path 15, the sample separated by the electrophoresis is detected. The detection of the sample can be carried out by such a method as absorptiometric method, fluorometric method, electrochemical method, conductimetric method, or the like.

The electrophoresis buffer is supplied to the respective reservoirs 17c, 17s' and the wastes 17a, 17w. A buffer solution such as TTE (50 mM Tris/50 mM TAPS/2 mM EDTA) or TBE (90 mM Tris/64.6 mM boric acid/2.5 mM EDTA) can be used as the electrophoresis buffer. Since the buffer solution is inexpensive and can be easily adjusted, the reservoirs 17c, 17s' and the wastes 17a, 17w can have large capacities to thereby reduce the effect of the electrolysis, so that an amount of the solution enough for filling the flow paths 13, 15 can be secured.

The sample is introduced into the sample reservoir 22. Since the sample reservoir 22 is disposed separately from the buffer reservoir 17s' provided with the electrode, securing conductivity between the sample and the electrode is not an issue, and the sample can be provided in a small amount.

Since the sample reservoir 22 is not provided with the electrode, an upper surface of the sample reservoir 22 can be easily sealed by a member such as, for example, a plate-like silicone rubber, thereby preventing the evaporation of the sample.

FIGS. 2(A) and 2(B) show the second embodiment of the invention. FIG. 2(A) is a schematic plan view of the second embodiment, and FIG. 2(B) is a sectional view taken along line 2(B)—2(B) in FIG. 2(A). In the second embodiment, a plurality of separation flow paths 15-1 to 15-N is formed in an electrophoresis chip 31. Respective separation flow paths 15-1 to 15-N are provided with sample introduction flow paths 13-1 to 13-N that cross the separation flow paths 15-1 to 15-N, respectively. One end of each of the sample introduction flow paths 13-1 to 13-N is connected to a common loading buffer reservoir 27s' via through holes 24s. The other end of the sample introduction flow paths 13-1 to 13-N is connected to a common loading buffer waste 27w via through holes 24w. Sample reservoirs 22-1 to 22-N are respectively disposed at the sample introduction flow paths 13-1 to 13-N. The sample reservoirs 22-1 to 22-N are positioned at upper stream sides (a loading buffer reservoir 27s' side) of respective intersecting portions 19-1 to 19-N, where the sample introduction paths 13-1 to 13-N cross the separation flow paths 15-1 to 15-N, and the sample reservoirs 22-1 to 22-N are situated near the intersecting portions 19-1 to 19-N.

Respective ends of the separation flow paths 15-1 to 15-N are connected to a common separation buffer reservoir 27c via through holes 24c, and the other ends of the separation flow paths 15-1 to 15-N are connected to a common separation buffer waste 27a via through holes 24a.

The common buffer reservoirs 27s', 27c and the common buffer wastes 27w, 27a are respectively provided with electrodes 6, 4, 8, 2. The electrodes 2, 4, 6, 8 may be structured separately from the electrophoresis chip, so that the electrodes may be disposed in the electrophoresis device and detachably inserted into the chip. Alternatively, the electrodes may be fixed to the chip by the vapor deposition.

In the second embodiment, the separation medium is injected respectively into the separation flow paths 15-1 to 15-N and the sample introduction flow paths 13-1 to 13-N, and the buffer is injected into the buffer reservoirs 27s', 27c and the buffer wastes 27w, 27a to be in contact with the electrodes 6, 4, 8, 2. The sample is respectively injected into the sample reservoirs 22-1 to 22-N, and the predetermined voltage is applied via the electrodes 2, 4, 6, 8, so that the sample is introduced into the intersecting portions 19-1 to 19-N where the flow paths cross. Thereafter, by switching the applied voltage, the sample is allowed to migrate along the separation flow paths 15-1 to 15-N by the electrophoresis to be separated therein, and detected at the predetermined position.

According to the second embodiment shown in FIGS. 2(A) and 2(B), regardless of the number of the separation flow paths 15-1 to 15-N, the buffer reservoirs 27s', 27c and the buffer wastes 27w, 27a are respectively used in common, that is, there can be provided the common buffer reservoir 27s', the common buffer reservoir 27c, the common buffer waste 27w, and the common buffer waste 27a. Therefore, the electrophoresis in a plurality of the separation flow paths 15-1 to 15-N can be achieved using four electrodes 2, 4, 6, 8, so that the electrophoresis device can be simplified.

FIGS. 3(A) and 3(B) show a modified example of the second embodiment. FIG. 3(A) is a schematic plan view thereof, and FIG. 3(B) is a sectional view taken along line 3(B)—3(B) in FIG. 3(A). In this embodiment, electrodes 6a, 4a, 8a, 2a respectively disposed in the common buffer reservoirs 27s', 27c and the common buffer wastes 27w, 27a are formed in such shapes that the electrodes 6a, 4a, 8a, 2a are respectively located away from the corresponding through holes 24s, 24c, 24w, 24a in a plurality of the flow paths with an equal distance. As a result, a voltage drop in the buffer from the electrode to the through hole is constant, so that an equal voltage in the respective flow paths is applied.

In the present invention, the sample reservoir for injecting the sample therein does not include the electrode, and the voltage for introducing the sample is applied by the electrode disposed at the portion other than the sample reservoir. Therefore, both reducing the amount of the sample and eliminating the effect of the electrolysis can be achieved.

In the case that the present invention is applied to the chip type electrophoresis device including a sample introduction path joining the separation flow path, it is easy to dispose the sample reservoir in the vicinity of the intersecting portion where the separation flow path and the sample introduction flow path cross each other, so that the sample can be introduced efficiently.

In the case that the single chip type member is provided with a plurality of the separation flow paths to which the electrode is connected in common, the electrophoresis device can be simplified.

While the invention has been explained with reference to the specific embodiments of the invention, the explanation is illustrative and the invention is limited only by the appended claims.

What is claimed is:

1. A chip type electrophoresis device for analyzing a sample, comprising:
    a chip member,
    a separation flow path formed in the chip member and having two ends,
    a sample introduction flow path formed in the chip member and having two ends, said sample introduction flow path intersecting the separation flow path,
    a sample reservoir that does not contain an electrode disposed in the chip member and connected to the sample introduction flow path at a position other than the two ends thereof for injecting the sample to the sample introduction flow path, and
    electrodes provided at the two ends of the sample introduction flow path for applying a voltage to the sample reservoir without providing an electrode to the sample reservoir.

2. A chip type electrophoresis device according to claim 1, further comprising two electrodes attached to the two ends of the separation flow path.

3. A chip type electrophoresis device according to claim 1, wherein said chip member further includes a plurality of separation flow paths connected to electrodes, said electrodes being arranged in common for the separation flow paths.

4. A chip type electrophoresis device according to claim 3, wherein said chip member further includes a plurality of introduction flow paths with ends and electrodes attached to the ends of the introduction flow paths, said electrodes in the introduction flow paths being arranged in common.

5. A chip type electrophoresis device according to claim 4, further comprising reservoirs connected to the separation flow paths in common and the introduction flow paths in common.

6. A chip type electrophoresis device according to claim 1, wherein said chip member is formed of two plates, said separation flow path and said introduction path being formed in one of the two plates and said sample reservoir being formed in one of the two plates.

7. A chip type electrophoresis device for analyzing a sample, comprising:
    a chip member,
    a separation flow path formed in the chip member and having two ends,
    a sample reservoir that does not contain an electrode disposed in the chip member and connected to the separation flow path at a position other than the two ends thereof for injecting the sample therein,
    electrodes provided at the two ends of the separation flow path for applying a voltage to the sample reservoir without providing an electrode to the sample reservoir, and
    a plurality of separation flow paths connected to the electrodes, said electrodes being arranged in common for the separation flow paths.

8. A chip type electrophoresis device according to claim 7, further comprising reservoirs connected to the separation flow paths in common.

* * * * *